United States Patent
Woo et al.

(10) Patent No.: US 10,830,749 B1
(45) Date of Patent: Nov. 10, 2020

(54) METHOD AND APPARATUS FOR MULTIPLE VISCOSITY AND FREEZE POINT MEASUREMENTS ON THE SAME ALIQUOT AND THE DETERMINATION OF TEMPERATURE AT ANY SPECIFIED VISCOSITY ABOVE THE FREEZE POINT

(71) Applicants: Edmund K. H. Woo, Richmond (CA); Shinya Matsueda, Richmond (CA); Vivian Hoi Nga Yuen, Vancouver (CA); Gordon S. Y. Chiu, Richmond (CA); Charles Yam Chuen Tsang, Vancouver (CA)

(72) Inventors: Edmund K. H. Woo, Richmond (CA); Shinya Matsueda, Richmond (CA); Vivian Hoi Nga Yuen, Vancouver (CA); Gordon S. Y. Chiu, Richmond (CA); Charles Yam Chuen Tsang, Vancouver (CA)

(73) Assignee: Phase Analyzer Company, Richmond (CA)

( * ) Notice: Subject to any disclaimer, the term of this patent is extended or adjusted under 35 U.S.C. 154(b) by 616 days.

(21) Appl. No.: 15/642,650

(22) Filed: Jul. 6, 2017

Related U.S. Application Data

(60) Provisional application No. 62/359,495, filed on Jul. 7, 2016.

(51) Int. Cl.
| | |
|---|---|
| *G01F 17/00* | (2006.01) |
| *G01N 33/22* | (2006.01) |
| *G01N 11/04* | (2006.01) |
| *G01N 11/00* | (2006.01) |

(52) U.S. Cl.
CPC ............ *G01N 33/22* (2013.01); *G01N 11/04* (2013.01); *G01N 2011/002* (2013.01)

(58) Field of Classification Search
CPC ... G01N 33/22; G01N 11/04; G01N 2011/002
USPC .......................................................... 702/50
See application file for complete search history.

(56) References Cited

U.S. PATENT DOCUMENTS

| | | | | |
|---|---|---|---|---|
| 2003/0193989 | A1* | 10/2003 | Tsang ..................... | G01N 25/04 374/16 |
| 2011/0126614 | A1* | 6/2011 | Belitsch ................. | G01N 11/04 73/54.04 |
| 2014/0250983 | A1* | 9/2014 | Spino ..................... | G01N 11/14 73/54.43 |

OTHER PUBLICATIONS

Korsten, Viscosity of Liquid Hydrocarbons and Their Mixtures, AIChE Journal, vol. 47, No. 2, pp. 453-462. (Year: 2001).*

* cited by examiner

*Primary Examiner* — Sujoy K Kundu
*Assistant Examiner* — Xiuqin Sun
(74) *Attorney, Agent, or Firm* — John J. Elnitski, Jr.

(57) ABSTRACT

An integrated test device adapted to perform tests on a single aliquot of a liquid sample. The test device includes a viscosity test cell adapted to perform viscosity tests on the liquid sample; a freeze point test cell adapted to perform freeze point tests on the liquid sample; a sample injection port adapted to load the single aliquot of the liquid sample into both of the viscosity test cell and the freeze point test cell, where the viscosity test cell and the freeze point test cell are connected in parallel to the sample injection port; a data processing unit to collect data from the viscosity test cell and the freeze point test cell and process the data, the data processing unit performing calculations to determine temperatures at any specified viscosity above a freeze point and checks of integrity of the viscosity measurements.

15 Claims, 3 Drawing Sheets

METHOD AND APPARATUS FOR MULTIPLE VISCOSITY AND FREEZE POINT MEASUREMENTS ON THE SAME ALIQUOT AND THE DETERMINATION OF TEMPERATURE AT ANY SPECIFIED VISCOSITY ABOVE THE FREEZE POINT

This application claims the benefit of and incorporates by reference U.S. Provisional Application No. 62/359,495, filed Jul. 7, 2016.

BACKGROUND

The present invention generally relates to determine the cold flow characteristics of fuels. More specifically, the present invention relates to the measurement of freeze point and multiple viscosities of fuel.

Airlines use the polar routes to save fuel and flight time. According to a study by Nav Canada and the Federal Aviation Authority of Russia (FAAR) in 2009, flight time can be cut by two hours if the polar routes are used instead of the traditional ones. There is a ten-fold increase in traffic on the polar routes from 2003 to 2010 (from 884 to 9683 flights), according to statistics from Nav Canada.

The auxiliary power unit (APU) is a critical safety device for polar flights and ETOPS (extended operations, also known as EDTO or extended diversion time operations), as it provides power to start the main engines, and supplies backup electricity and compressed air if the engine fails. APUs that are ETOPS-compliant must be able to start and operate over the entire flight envelope, which may entail altitude at more than 40000 ft, or from a complete cold-soak condition for up to 15 hours. APUs do not have inlet fuel-oil heat exchanger, so cold fuel is directed to inlet filter.

The low temperature operation of the APU is limited by both the aviation fuel freeze point and viscosity. Freeze point information is required for preventing the fuel from freezing. Viscosity data is needed to ensure proper atomization and spray pattern are achieved for reliable starting of the APUs. According to the Aviation Rulemaking Advisory Committee (ARAC), main engines and APUs are designed to start and operate up to a maximum fuel kinematic viscosity of 12 cSt (or mm2/s) at the operating temperature. cSt stands for centistoke and is a kinematic viscosity measurement unit, where cSt=1 $mm^2/s$.

The current American Society for Testing and Materials (ASTM) Standard D1655, titled Standard Specification for Aviation Turbine Fuels, specifies 8 cSt at –20° C. as the maximum kinematic viscosity for Jet A and Jet A-1 fuels. However, the actual operating temperature of polar flights is usually much lower than –20° C. and can be very close to the freeze point of the fuels. According to ASTM D1655, the freeze point specification for Jet A is –40° C. and for Jet A-1 is –47° C. Studies have shown that some aviation fuels could reach 12 cSt at –30° C. To ensure reliable starting and operation of the APU, it is therefore critically important to determine the aviation fuel freeze point, the kinematic viscosity near the freeze point, as well as the temperature at which the 12 cSt kinematic viscosity limit is reached.

Visual methods such as ASTM D445 (Standard Test Method for Kinematic Viscosity of Transparent and Opaque Liquids) are impractical for measuring low temperature viscosities due to a variety of technical difficulties, for example, condensation and insufficient cooling capacity. Visual methods are also not reliable in determining whether liquid-solid two phase exist because it is difficult to see the small crystals and to distinguish between the hydrocarbon and ice crystals. Viscosity measurements are meaningful and should only be determined for single phase liquids.

The viscometer described in U.S. Pat. No. 8,806,921, issued on Aug. 19, 2014 to Gosling et al., is a capillary assembly connected to a sample reservoir, an air drying apparatus, a pump for advancing the liquid sample, and an apparatus for controlling the liquid sample temperature at above and/or below 0° C. It determines the temperature of a predetermined viscosity by iteratively changing the liquid sample temperature until the viscosity at the predetermined level is reached. This temperature scanning method is tedious and impractical, and is not able to determine whether the sample remains as a single phase liquid or has already entered into the liquid-solid two-phase region at low temperatures.

Another viscometer described in US. Pat. No. 2014/0250983, issued on Sep. 11, 2014 to Spino et al., is an oscillating piston-type viscometer with a chiller that can change the temperature of the fluid being measured. It measures fluid viscosity continuously from ambient to low temperatures. The data is used to calculate an approximate temperature-viscosity curve, which is then used for predicting the pumpability limit of the fluid and for calculating the freeze point and pour point. It measures only the dynamic viscosity but not the kinematic viscosity. The freeze and pour points are only derivation from the features of an approximate temperature-viscosity curve and not direct measurement. The derivation has not been tested or approved, or correlated with any established method. It is time consuming to continuously measure the viscosity as temperature is lowered and to derive the other properties from the data.

The viscometer described in U.S. Pat. No. 7,131,318, issued on Nov. 7, 2006 to Tsang et al., consists of a capillary tube embedded in a thermal block which temperature is controlled by a thermoelectric device. Dynamic viscosity is determined by measuring the flow velocity of the test specimen under a controlled constant drive pressure with flow sensors. Density is measured with a commercially available density meter which allows the kinematic viscosity to be calculated. This viscometer is compact and robust, and allows the measurement of both dynamic and kinematic viscosities in one test sequence. The method is implemented into ASTM D7945, titled Determination of Dynamic Viscosity and Derived Kinematic Viscosity of Liquids by Constant Pressure Viscometer.

Light scattering method has been used for measuring freeze point and cloud point. Such method is described in U.S. Pat. No. 5,088,833 issued on Feb. 18, 1992 to Tsang et al. and implemented into ASTM D5972 (Standard Test Method for Freezing Point of Aviation Fuels (Automatic Phase Transition Method)), which is a well-accepted method for FP measurement and is included in the ASTM D1655 specification for aviation fuels.

In the past, kinematic viscosity specification is at a warmer temperature because of the difficulty in viscosity measurement at low temperatures and the concern of infringing the liquid-solid two phase coexistence region at temperatures below the freeze point. With the advance of new technologies, low temperature viscosities can now be measured; however, none of these measurements can verify whether the sample being tested is in the single-phase Newtonian liquid region. Freeze point data thus becomes essential for verifying the integrity of viscosity measurements.

It is an object of the present invention to provide an integrated device that simultaneously measures freeze point and multiple viscosities, both dynamic and kinematic, with a single aliquot of sample, based upon a combination of ASTM D7945 and D5972.

Moreover, it is an object of the present invention to provide a method that verifies the integrity of the viscosity measurements and determines the temperature at any specified viscosity above the freeze point, based upon the Walther-McCoull equation in ASTM D341 (Standard Practice for Viscosity-Temperature Charts for Liquid Petroleum Products). It is also an object of the present invention to inform the temperature at a specified viscosity if and only if the temperature is above the freeze point whereby the sample remains in Newtonian single-phase liquid regime.

SUMMARY OF THE INVENTION

An integrated test device adapted to perform tests on a single aliquot of a liquid sample. The test device includes a viscosity test cell adapted to perform viscosity tests on the liquid sample; a freeze point test cell adapted to perform freeze point tests on the liquid sample; a sample injection port adapted to load the single aliquot of the liquid sample into both of the viscosity test cell and the freeze point test cell, where the viscosity test cell and the freeze point test cell are connected in parallel to the sample injection port; a data processing unit to collect data from the viscosity test cell and the freeze point test cell and process the data, the data processing unit performing calculations to determine temperatures at any specified viscosity above a freeze point and checks of integrity of the viscosity measurements.

DETAILED DESCRIPTION

The present invention provides an integrated test device for freeze point and multiple viscosity measurements with a single aliquot of sample in one test sequence. The viscosity measurements using the test device include both the dynamic and kinematic viscosities. The test device can also verify the integrity of the viscosity measurements and determine the temperature at any specified viscosity above the freeze point. A single aliquot is a single instance of sampling. Using a single aliquot means that once a quantity of sample is introduced into the test device, that particular introduced sample will be used to determine multiple quantities such as freezing point, density, and viscosity. This provides for almost no chance of sample confusion or mixup. If only a single aliquot is used, then whatever values obtained are all derived from the same amount of sample. On the other hand, if multiple aliquots are used, then there is always the opportunity of using the wrong samples. The test device can determine the temperature at any viscosity of interest, where temperature at 12 cSt is the standard used in the aviation industry. The determination of the temperature at any specified viscosity is based upon the Walther-Mc-Coull equation as described in ASTM D341. The test device can assess the relative magnitude of the freezing point with respect to the calculated temperature at a specified viscosity of interest and make a determination of the freeze point temperature of the sample using a sample. So at the conclusion of both tests, the first test then "informs" the second test of the actual freezing point. If the first test is colder than the result of the second test, then the second result is meaningful, i.e. viscosity result is obtained at a temperature when the sample is all liquid. If the freeze point is warmer than the result of the second test, then the second result would not be reported.

Figure 1:
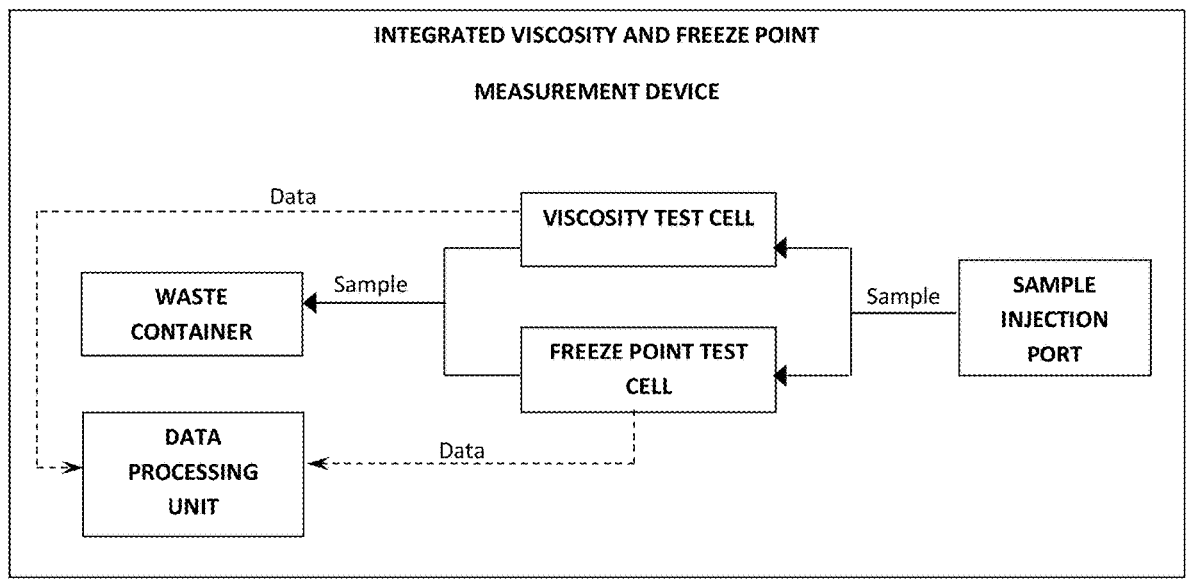
FIG. 1 is a block diagram of a integrated test device according to the present invention.

FIG. 1 shows a block diagram of the test device of the present invention. The device includes a sample injection port that loads a sample into two test cells that are connected in parallel. The two test cells are a viscosity test cell and freeze point test cell. The viscosity test cell is the viscometer, as described in ASTM D7945. The freeze point test cell is the apparatus, as described in ASTM D5972. The viscosity test cell and freeze point test cell receive the sample from the sample injection port, perform the tests and then discharge the sample to the waste container. The two test cells are connected in parallel to perform freeze point and viscosity tests simultaneously. The test device includes a data processing unit that collects information from the viscosity test cell and freeze point test cell. The data processing unit performs calculations to determine the temperatures at any specified viscosity above the freeze point and checks the integrity of the viscosity measurements.

The viscosity test cell receives part of the sample from the sample injection port to measure multiple viscosities of the sample at specified temperatures. The viscosity test cell includes the ability to discharge the sample to a waste container. The sample is injected into a temperature-controlled horizontal capillary tube of the viscosity test cell where a regulated gas pressure drives the sample in the forward direction. The times of transit of the sample across marked segments are measured by a series of sensors.

Numerical values of the pressures and times of transit are transferred to the data processing unit. Dynamic viscosities of the sample can then be calculated using both sets of data according to the Hagen-Poiseuille principle. The viscosity test cell measures the density and multiple dynamic viscosities of the sample at specified temperatures, such as at −20° C. and −40° C. for aviation fuels. The freeze point test cell receives part of the sample from the sample injection port to measure freeze point of the sample. The freeze point test cell includes the ability to discharge the sample to the waste container. The sample is cooled rapidly in the freeze point test cell until crystallization is observed to take place using light scattering. Thereafter, the sample is warmed at a pre-determined rate until all of the solid crystals are detected to melt and return to the liquid state. The entire sequence of temperature vs. scattered light signal values are transferred to the data processing unit where the freezing point is determined.

The data processing unit collects data from the freeze point and viscosity test cells. The following data is collected from respective test cells and transferred to the data processing unit. The data collected from the freeze point test cell is the temperature of the sample and scattered light signal at corresponding temperatures. The data collected from the viscosity test cell is pressure of driving gas as it pushes the sample across marked segments and times when the sample is detected to cross the marked segments. A density test cell is part of the viscosity test cell that measures the density of the sample and transfer the results to the data processing unit. For example for aviation fuels, the data processing unit calculates the kinematic viscosities at −20° C. and −40° C. with the following equation:

kinematic viscosity (KV)=dynamic viscosity/density of the liquid

The data processing unit also calculates the temperature at any specified viscosity, such as 12 cSt for aviation fuels, by substituting the kinematic viscosities at −20° C. and −40° C. into the Walther-McCoull equation, as described in ASTM D341:

$$\log \log(v+0.7)=A+B \log T,$$

where v is the kinematic viscosity and T is the temperature in Kelvin. The data processing unit then solves for the coefficients A and B in the equation for at least two calculated viscosity values at corresponding temperatures. The temperature at 12 cSt can then be calculated with the inverse of the Walther-McCoull equation.

Figure 2:
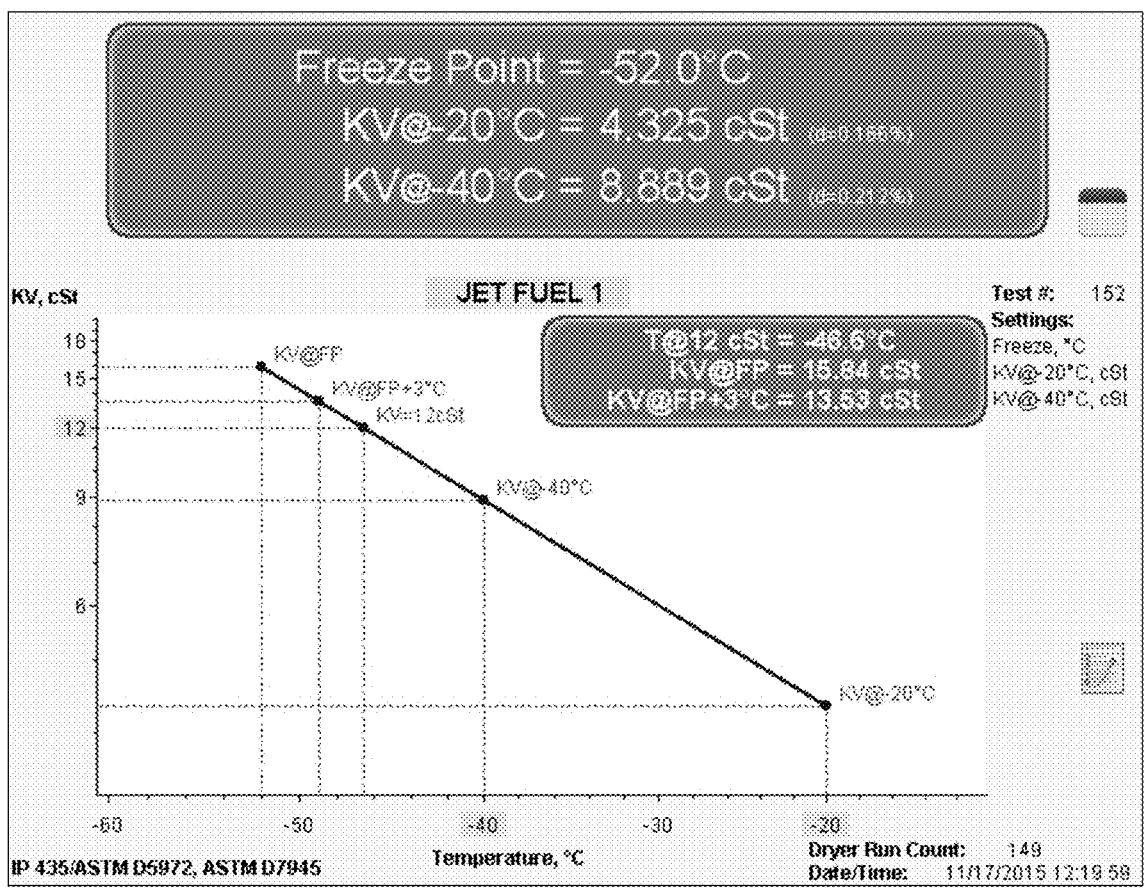
FIG. 2 is a data plot of results using the integrated test device according to the present invention.

FIG. 2 shows results obtained in testing aviation fuel using the integrated test device. Prior to the test, the previous test sample was automatically flushed out of the sample paths with air. Then, a glass vial of the about 25 mL of the new test sample is placed at the sample injection port. The sample is automatically flushed through the integrated device to clean the sample paths. Air is then purged through the paths to keep them dry. Once the sample paths are clean and dry, more of the test sample is loaded into the viscosity and freeze point test cells, where the viscosity and freeze point are measured. The data processing unit collects and displays the test data, as shown in the top rectangular box in FIG. 2. The freeze point of the aviation fuel is shown to be −48.7° C., KV at −20° C. is 5.389 cSt, KV at −40° C. is 11.78 cSt, and density at 15° C. is 0.8176 g/mL. The temperature at 12 cSt and the KV at freeze point are calculated and displayed in the smaller rectangular box at the middle of FIG. 2. The temperature at 12 cSt of the aviation fuel is −40.4° C., which is warmer than its freeze point. The KV at freeze point is 18.33 cSt. The sample is in the single-phase Newtonian liquid region at any temperature above its freeze point of −48.7° C. This means the −20° C. and −40° C. viscosity measurements and the temperature at 12 cSt calculation for this sample are all valid. A graphical presentation of the test results is also shown in FIG. 2.

Figure 3:
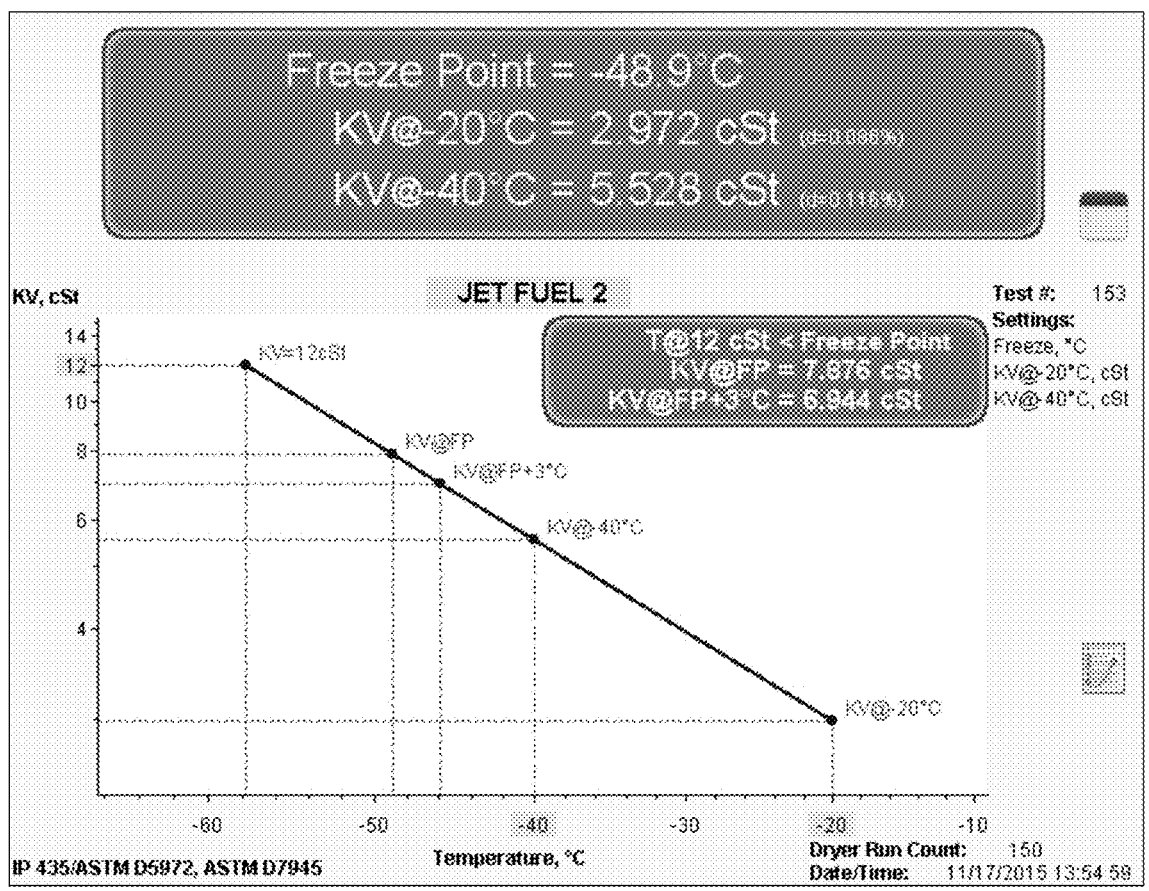
FIG. 3 is a data plot of results using the integrated test device according to the present invention.

FIG. 3 shows results obtained in testing another aviation fuel using the integrated test device. The freeze point of the aviation fuel is −50.8° C., KV at −20° C. is 3.596 cSt, KV at −40° C. is 6.998 cSt, and density at 15° C. is 0.7981 g/mL. The temperature at 12 cSt of the aviation fuel is calculated to be colder than its freeze point. The KV at freeze point is 11.22 cSt. The sample is in the single-phase Newtonian liquid region only at temperatures above its freeze point of −50.8° C. This means the −20° C. and −40° C. viscosity measurements are valid. It is also expected that the KV of the sample would reach 12 cSt after entering the liquid-solid two phase region, in which case the calculation of temperature at 12 cSt has extended into a non-single-phase region for which the interpretation of kinematic viscosity is not meaningful. In this case the temperature at 12 cSt is not delineated but instead indicated to be colder than the freezing point. A graphical presentation of the test results is also shown in FIG. 3.

The testing device is capable of measuring all of the quantities, where these quantities are considered independent and unrelated, therefore they are typically measured separately. The testing device measures all of the quantities using a single aliquot, thereby relieving a human operator of attending to multiple machines, removing potential sample mixup, and perhaps most importantly, to apply meaningful interpretation of one result of the freezing point to another result of the viscosity. The concept is the use of viscosity, insofar as it gives an indication of the ability of a liquid to flow that is only meaningful when the liquid remains in a single phase, namely all liquid without any solid components, and such is true when the liquid of the test sample is warmer than the freezing point. The test device and method is that a report of temperature corresponding to a pre-specified viscosity value is done so only when the temperature is warmer the freezing point of the liquid, thereby ensuring that the liquid is still in single phase. This is in contrast to other methods to measure viscosity at cold temperatures. A value may be measured, but is that value meaningful in the sense that the liquid is free of solids? The testing device and method is that by including freezing point as part of the overall consideration, the report that a sample reaches a pre-specified viscosity at a certain temperature, warmer than the freezing point, is physically meaningful. If the determined temperature is colder than the freezing point, viscosity loses its meaning, and it is not reported.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

We claim:

1. An integrated test device adapted to perform tests on a single aliquot of a liquid sample comprising:
   a viscosity test cell adapted to perform viscosity tests on the liquid sample;
   a freeze point test cell adapted to perform freeze point tests on the liquid sample, that is separate and independent of said viscosity test cell;
   a sample injection port adapted to load the single aliquot of the liquid sample simultaneously into both of said viscosity test cell and said freeze point test cell, where said viscosity test cell and said freeze point test cell are connected in parallel to said sample injection port;
   a data processing unit to collect data from said viscosity test cell and said freeze point test cell and process said data, said data processing unit performing calculations to determine temperatures at any specified viscosity above a freeze point and checks of integrity of the viscosity measurements.

2. The integrated test device of claim 1, wherein said viscosity test cell includes sensors to provide data to said data processing unit that includes pressure data of driving gas as the gas pushes the liquid sample in said viscosity test cell across marked segments and time data when the sample is detected to cross the marked segments.

3. The integrated test device of claim 1, wherein said freeze point test cell includes sensors to provide data to said data processing unit that includes temperature data of the sample in said freeze point test cell and scattered light signal data at corresponding temperatures.

4. The integrated test device of claim 3, wherein said data processing unit calculates the kinematic viscosities with a first equation of kinematic viscosity (KV)=dynamic viscosity/density of the liquid for a temperature range and also calculates temperature at any specified viscosity by substituting said calculated kinematic viscosities of said temperature range into a second equation $\log \log(\square+0.7)=A+B \log T$, where $\square$ is the kinematic viscosity and T is the temperature in Kelvin and wherein said data processing unit then solves for the coefficients A and B in the equation for at least two calculated viscosity values at corresponding temperatures, finally a temperature at specific viscosity is calculated with the inverse of said second equation.

5. The integrated test device of claim 1, wherein said viscosity test cell includes a density test cell as part of said viscosity test cell to measures density of the sample and transfer results to said data processing unit.

6. The integrated test device of claim 1, wherein said viscosity test cell is as described in ASTM D7945 and said freeze point test cell is an apparatus as described in ASTM D5972.

7. The integrated test device of claim 1, wherein aviation fuel is the liquid sample.

8. A method for measuring multiple viscosities and freeze point of a sample, verifying the integrity of the viscosity measurements and calculating the temperature at any specified viscosity above the freeze point for the sample, comprising:
   loading a sample into a sample injection port;
   loading the sample from the sample injection port into a viscosity test cell and a freeze point test cell that are connected in parallel to the sample injection port, where the viscosity test cell and the freezepoint test cell are separate and independent of each other to allow simultaneous testing of the sample;
   measuring multiple viscosities of the sample at specified temperatures using the viscosity test cell;
   measuring freeze point of the sample using the freeze point test cell;
   measuring density of the sample; and
   collecting data from the viscosity test cell and the freeze point test cell, calculating temperatures at any specified viscosity above the freeze point and checking the integrity of the viscosity measurements using a data processing unit.

9. The method of claim 8, wherein the data is collected the freeze point test cell is different temperatures of the sample and scattered light signal data at corresponding temperatures and wherein the data collected from the viscosity test cell is pressure of driving gas as it pushes the sample across marked segments and times when the sample is detected to cross the marked segments.

10. The method of claim 8, wherein the data processing unit calculates the kinematic viscosities with a first equation of kinematic viscosity (KV)=dynamic viscosity/density of the liquid for a temperature range and also calculates temperature at any specified viscosity by substituting said calculated kinematic viscosities of said temperature range into a second equation $\log \log(\square+0.7)=A+B \log T$, where $\square$ is the kinematic viscosity and T is the temperature in Kelvin and wherein the data processing unit then solves for the coefficients A and B in the equation for at least two calculated viscosity values at corresponding temperatures, finally a temperature at specific viscosity is calculated with the inverse of the second equation.

11. The method of claim 8, wherein prior to loading the sample to be tested, the sample injection port, the viscosity test cell and the freeze point test cell are flushed out air, a preloading amount of the sample is loaded into the sample injection port, the preloading amount of the sample is flushed through the sample injection port, the viscosity test cell and the freeze point test cell to clean sample paths in the sample injection port, the viscosity test cell and the freeze point test cell, air is purged through the paths to keep them dry.

12. The method of claim 8, wherein said sample is of a single aliquot.

13. The method of claim 8, wherein said sample is of aviation fuel.

14. The method of claim 8, wherein calculating the temperature at any specified viscosity is a fixed kinematic viscosity.

15. The method of claim 14, wherein the fixed kinematic viscosity is 12 cSt.

* * * * *